United States Patent [19]

Peery et al.

[11] Patent Number: 5,712,108
[45] Date of Patent: Jan. 27, 1998

[54] PEPTIDOGLYCAN BIOSYNTHETIC MURE PROTEIN FROM STREPTOCUCCUS PNEUMONIAE

[75] Inventors: Robert Brown Peery, Brownsburg; Paul Luther Skatrud, Indianapolis, both of Ind.

[73] Assignee: Eli Lilly and Company, Indianapolis, Ind.

[21] Appl. No.: 655,114

[22] Filed: May 29, 1996

[51] Int. Cl.$^6$ ............................................. C12N 9/00
[52] U.S. Cl. ................................. 435/15; 435/183
[58] Field of Search ............................ 435/183, 15

[56] References Cited

PUBLICATIONS

Daniel, Richard A., et al., *J. of General Microbiology*, 139:361–370 (1993).

Michaud, Catherine, et al., *Eur. J. Biochem.*, 194:853–861 (1990).

Tao, Jing–Song, et al., *Can. J. Microbiol.*, 35, 1051–1054 (1989).

Jacobs, M.R. (1992) Treatment and Diagnosis of Infections Caused by Drug–Resistant *Streptococcus pneumoniae*, Clin. Infect. Dis. 15: 119–127, Jan. 1992.

Flouret, B. et al. (1981) Reverse–Phase High–Pressure Liquid Chromatography of Uridine Diphosphate N–Acetylmuramyl Peptide Precursors of Bacterial Cell Wall Peptidoglycan, Anal. Biochem. 114: 59–63, Jan. 1981.

*Primary Examiner*—Robert A. Wax
*Assistant Examiner*—Einar Stole
*Attorney, Agent, or Firm*—Thomas D. Webster; David E. Boone

[57] ABSTRACT

The invention provides isolated nucleic acid compounds encoding the murE stem peptide biosynthetic gene of *Streptococcus pneumoniae*. Also provided are vectors and transformed heterologous host cells for expressing the murE enzyme product and a method for identifying compounds that inhibit stem peptide biosynthesis.

5 Claims, 1 Drawing Sheet

PEPTIDOGLYCAN BIOSYNTHETIC MURE PROTEIN FROM STREPTOCUCCUS PNEUMONIAE

BACKGROUND OF THE INVENTION

This invention relates to recombinant DNA technology. In particular the invention pertains to the cloning of the murE gene encoding uridine-diphosphate-N-acetylmuramoyl-L-alanyl-D-glutamate: L-lysine ligase of Streptococcus pneumoniae and the use of the murE gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in Streptococcus pneumoniae which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that many such compounds have low toxicity in humans and potentially high therapeutic value.

The bacterial cell wall structure comprises a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinks step the peptidoglycan structure is severely weakened and susceptible to degradation. Indeed, it is this crosslinking step that has been a frequently targeted site for antibiotic compounds such as the beta-lactam antibiotics.

In contrast to the beta-lactam case, which targets the crosslinking step, the pathway involved in the synthesis of the stem peptide has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by N-acetylmuramate:L-alanine ligase; UDP-N-acetyl-muramoyl-L-alanine:D-glutamate ligase; UDP-N-acetyl-muramoyl-L-alanyl-D-glutamate:lysine ligase; UDP-N-acetylmuramoyl-L-alanyl-D-glutamyl-L-lysine:D-alanyl-D-alanine ligase; and D-alanyl-D-alanine synthetase, the final product, UDPMurNAc-L-Ala-D-Glu-L-lysine-D-Ala-D-Ala, is produced in Streptococcus pneumoniae.

The enzymatic steps involved in the formation of the stem peptide are potentially a rich source for new antibacterial targets. A few inhibitors, which target this pathway, have been developed. For example, D-cycloserine, inhibits the alanine racemase and the D-alanine-D-alanine synthetase; phosphonomycin inhibits UDP-GlcNac conversion to UDP-GlcNac-enolpyruvate; and Ala-phosphonine inhibits the addition of L-Alanine in the formation of UDP-MurNac-L-Ala.

The genes directly involved with assembly of the stem peptide in Escherichia coli have been cloned and characterized. These genes occur in two clusters on the E. coli chromosome. Analogous genes have been cloned from Bacillus subtilus, and from Haemophilus influenzae (Fleischmann et al., Science, 269:496–512 (1996).

While inroads in the development of new antibiotics and new targets for antibiotic compounds have been made with a variety of microorganisms, progress has been less apparent in Streptococcus pneumoniae. In part, Streptococcus pneumoniae presents a special case because the organism is highly mutagenic and readily takes up exogenous DNA from its surroundings. Thus, the need for new antibacterial compounds and new targets for antibacterial therapy is especially acute in Streptococcus pneumoniae.

SUMMARY OF THE INVENTION

The present invention is designed to meet the aforementioned need and provides, inter alia, isolated nucleic acid molecules that encode the murE gene product from Streptococcus pneumoniae. The invention also provides the protein product of the Streptococcus pneumoniae murE gene, uridine-diphosphate-N-acetyulmuramoyl-L-alanyl-D-glutamate:L-lysine ligase (MurE protein), in substantially purified form.

Having the cloned murE gene of Streptococcus pneumoniae enables the production of large quantities of the cognate enzyme from which large scale screens can be developed to identify new antibacterial compounds targeted at the stem peptide biosynthetic pathway. It may be possible to combine several of the proteins involved in stem peptide biosynthesis in a single screen to examine several steps at the same time. The key proteins may be structurally analyzed such that structure-based drug design may be used to develop novel compounds effective in the treatment of antibiotic resistant mircroorganisms.

In one embodiment the present invention is a DNA molecule comprising the nucleotide sequence identified as SEQ ID NO. 1:

```
ATG AAT AAG ATT GAA ACC GTA TTA GAT ATT TTA AAG AAA GAT GGC CTT   48
Met Ile Lys Ile Glu Thr Val Leu Asp Ile Leu Lys Lys Asp Gly Leu
 1               5                  10                  15

TTT CGC GAA ATT ATT GAC CAA GGT CAT TAC CAC TAC AAC TAC AGC AAA   96
Phe Arg Glu Ile Ile Asp Gln Gly His Tyr His Tyr Asn Tyr Ser Lys
         20                  25                  30
```

-continued

```
GTT ATT TTT GAT AGC ATC AGC TAC GAC AGC CGA AAA GTA ACA GAA GAC    144
Val Ile Phe Asp Ser Ile Ser Tyr Asp Ser Arg Lys Val Thr Glu Asp
        35                  40                  45

ACT CTT TTT TTT GCA AAA GGC GCT GCC TTT AAA AAA GAA TAC CTT CTT    192
Thr Leu Phe Phe Ala Lys Gly Ala Ala Phe Lys Lys Glu Tyr Leu Leu
        50                  55                  60

TCT GCT ATA ACA CAA GGT TTA GCT TGG TAT GTA GCT GAA AAG GAC TAC    240
Ser Ala Ile Thr Gln Gly Leu Ala Trp Tyr Val Ala Glu Lys Asp Tyr
65                  70                  75                  80

GAA GTC GAT ATC CCT GTC ATC ATT GTG AAC GAT ATA AAG AAA GCC ATG    288
Glu Val Asp Ile Pro Val Ile Ile Val Asn Asp Ile Lys Lys Ala Met
                85                  90                  95

AGT TTG ATT GCC ATG GAG TTC TAT GGT AAT CCA CAA GAG AAA CTC AAA    336
Ser Leu Ile Ala Met Glu Phe Tyr Gly Asn Pro Gln Glu Lys Leu Lys
            100                 105                 110

CTC CTT GCC TTT ACT GGT ACT AAG GGT AAG ACA ACA GCA ACC TAT TTC    384
Leu Leu Ala Phe Thr Gly Thr Lys Gly Lys Thr Thr Ala Thr Tyr Phe
            115                 120                 125

GCC TAT AAC ATC TTA TCT CAA GGG CAT AGA CCT GCT ATG TTG TCG ACC    432
Ala Tyr Asn Ile Leu Ser Gln Gly His Arg Pro Ala Met Leu Ser Thr
        130                 135                 140

ATG AAC ACA ACT CTT GAT GGC GAG ACT TTC TTT AAG TCA GCG TTG ACA    480
Met Asn Thr Thr Leu Asp Gly Glu Thr Phe Phe Lys Ser Ala Leu Thr
145                 150                 155                 160

ACC CCT GAG AGT ATT GAC CTC TTT GAC ATG ATG AAT CAG GCT GCT CAA    528
Thr Pro Glu Ser Ile Asp Leu Phe Asp Met Met Asn Gln Ala Ala Gln
                165                 170                 175

AAT GAC CGT ACC CAC CTC ATC ATG GAA GTC TCC AGT CAA GCC TAT CTA    576
Asn Asp Arg Thr His Leu Ile Met Glu Val Ser Ser Gln Ala Tyr Leu
            180                 185                 190

GTC CAT CGA GTC TAT GGA CTG ACC TTT GAT GTA GGA GTC TTT CTT AAC    624
Val His Arg Val Tyr Gly Leu Thr Phe Asp Val Gly Val Phe Leu Asn
            195                 200                 205

ATC ACT CCT GAC CAT ATC GGC CCG ATT GAA CAC CCT AGC TTT GAA GAC    672
Ile Thr Pro Asp His Ile Gly Pro Ile Glu His Pro Ser Phe Glu Asp
        210                 215                 220

TAT TTc TAC CAC AAG CGT CTC TTG ATG GAA AAT AGC CGA GCA GTC ATC    720
Tyr Phe Tyr His Lys Arg Leu Leu Met Glu Asn Ser Arg Ala Val Ile
225                 230                 235                 240

ATT AAC AGT GAC ATG GAC CAC TTC TCA GTC TTG AAA GAA CAG GTT GAA    768
Ile Asn Ser Asp Met Asp His Phe Ser Val Leu Lys Glu Gln Val Glu
                245                 250                 255

GAT CAA GAC CAT GAT TTC TAT GGT AGC CAA TTT GAT AAC CAA ATC GAG    816
Asp Gln Asp His Asp Phe Tyr Gly Ser Gln Phe Asp Asn Gln Ile Glu
            260                 265                 270

AAT TCC AAA GCC TTT AGC TTT TCA GCT ACG GGT AAA CTC GCT GGA GAT    864
Asn Ser Lys Ala Phe Ser Phe Ser Ala Thr Gly Lys Leu Ala Gly Asp
        275                 280                 285

TAT GAT ATC CAA CTC ATT GGC AAC TTC AAC CAA GAA AAT GCA GTT GCT    912
Tyr Asp Ile Gln Leu Ile Gly Asn Phe Asn Gln Glu Asn Ala Val Ala
        290                 295                 300

GCT GGA CTT GCT TGT CTC CGT CTC GGA GCA AGT CTT GAG GAC ATC AAA    960
Ala Gly Leu Ala Cys Leu Arg Leu Gly Ala Ser Leu Glu Asp Ile Lys
305                 310                 315                 320

AAA GGC ATC GCT GCA ACC CGC GTT CCT GGT CGT ATG GAA GTC CTC ACT   1008
Lys Gly Ile Ala Ala Thr Arg Val Pro Gly Arg Met Glu Val Leu Thr
                325                 330                 335

CAG AAA AAT GGA GCC AAG GTC TTC ATC GAC TAT GCC CAC AAT GGG GAT   1056
Gln Lys Asn Gly Ala Lys Val Phe Phr Ile Asp Tyr Ala His Asn Gly Asp
            340                 345                 350

AGT CTG AAA AAA CTC ATC AAT GTG GTT GAA ACT CAT CAA ACC GGA AAG   1104
Ser Leu Lys Lys Leu Ile Asn Val Val Glu Thr His Gln Thr Gly Lys
        355                 360                 365
```

-continued

```
ATT GCT CTG GTT CTG GGA TCA ACA GGA AAC AAG GGA GAA AGT CGT CGT 1152
Ile Ala Leu Val Leu Gly Ser Thr Gly Asn Lys Gly Glu Ser Arg Arg
    370             375             380

AAG GAC TTT GGC CTC CTC CTC AAT CAA CAC CCT GAG ATT CAA GTC TTT 1200
Lys Asp Phe Gly Leu Leu Leu Asn Gln His Pro Glu Ile Gln Val Phe
385             390             395             400

CTG ACT GCT GAT GAC CCT AAC TAT GAA GAC CCA ATG GCC ATT GCA GAT 1248
Leu Thr Ala Asp Asp Pro Asn Tyr Glu Asp Pro Met Ala Ile Ala Asp
        405             410             415

GAA ATT AGT AGC TAC ATC AAT CAT CCT GTT GAA AAG ATT GCG GAT CGC 1296
Glu Ile Ser Ser Tyr Ile Asn His Pro Val Glu Lys Ile Ala Asp Arg
            420             425             430

CAA GAA GCC ATC AAG GCG GCA ATG GCT ATC ACA AAT CAC GAA TTA GAT 1344
Gln Glu Ala Ile Lys Ala Ala Met Ala Ile Thr Asn His Glu Leu Asp
            435             440             445

GCA GTT ATT ATT GCG GGT AAG GGA GCC GAT TGT TAC CAA ATC ATC CAG 1392
Ala Val Ile Ile Ala Gly Lys Gly Ala Asp Cys Tyr Gln Ile Ile Gln
    450             455             460

GGC AAG AAA GAA TCC TAC CCA GGA GAT ACA GCC GTC GCA GAA AAT TAT 1440
Gly Lys Lys Glu Ser Tyr Pro Gly Asp Thr Ala Val Ala Glu Asn Tyr
465             470             475             480

TTA                                                              1446
Leu
```

In another embodiment the present invention is a protein molecule comprising the sequence identified as SEQ ID NO. 2:

```
Met Ile Lys Ile Glu Thr Val Leu Asp Ile Leu Lys Lys Asp Gly Leu
1               5               10              15

Phe Arg Glu Ile Ile Asp Gln Gly His Tyr His Tyr Asn Tyr Ser Lys
            20              25              30

Val Ile Phe Asp Ser Ile Ser Tyr Asp Ser Arg Lys Val Thr Glu Asp
        35              40              45

Thr Leu Phe Phe Ala Lys Gly Ala Ala Phe Lys Lys Glu Tyr Leu Leu
    50              55              60

Ser Ala Ile Thr Gln Gly Leu Ala Trp Tyr Val Ala Glu Lys Asp Tyr
65              70              75              80

Glu Val Asp Ile Pro Val Ile Ile Val Asn Asp Ile Lys Lys Ala Met
            85              90              95

Ser Leu Ile Ala Met Glu Phe Tyr Gly Asn Pro Gln Glu Lys Leu Lys
        100             105             110

Leu Leu Ala Phe Thr Gly Thr Lys Gly Lys Thr Thr Ala Thr Tyr Phe
    115             120             125

Ala Tyr Asn Ile Leu Ser Gln Gly His Arg Pro Ala Met Leu Ser Thr
130             135             140

Met Asn Thr Thr Leu Asp Gly Glu Thr Phe Phe Lys Ser Ala Leu Thr
145             150             155             160

Thr Pro Glu Ser Ile Asp Leu Phe Asp Met Met Asn Gln Ala Val Gln
            165             170             175

Asn Asp Arg Thr His Leu Ile Met Glu Val Ser Ser Gln Ala Tyr Leu
        180             185             190

Val His Arg Val Tyr Gly Leu Thr Phe Asp Val Gly Val Phe Leu Asn
    195             200             205

Ile Thr Pro Asp His Ile Gly Pro Ile Glu His Pro Ser Phe Glu Asp
210             215             220

Tyr Phe Tyr His Lys Arg Leu Leu Met Glu Asn Ser Arg Ala Val Ile
225             230             235             240
```

-continued

| | | | | | | | | | | | | | | |
|---|---|---|---|---|---|---|---|---|---|---|---|---|---|---|
| Ile | Asn | Ser | Asp | Met 245 | Asp | His | Phe | Ser | Val 250 | Leu | Lys | Glu | Gln | Val 255 | Glu |
| Asp | Gln | Asp | His 260 | Asp | Phe | Tyr | Gly | Ser 265 | Gln | Phe | Asp | Asn | Gln 270 | Ile | Glu |
| Asn | Ser | Lys 275 | Ala | Phe | Ser | Phe | Ser 280 | Ala | Thr | Gly | Lys | Leu 285 | Ala | Gly | Asp |
| Tyr | Asp 290 | Ile | Gln | Leu | Ile | Gly 295 | Asn | Phe | Asn | Gln | Glu 300 | Asn | Ala | Val | Ala |
| Ala 305 | Gly | Leu | Ala | Cys | Leu 310 | Arg | Leu | Gly | Ala | Ser 315 | Leu | Glu | Asp | Ile | Lys 320 |
| Lys | Gly | Ile | Ala | Ala 325 | Thr | Arg | Val | Pro | Gly 330 | Arg | Met | Glu | Val | Leu 335 | Thr |
| Gln | Lys | Asn | Gly 340 | Ala | Lys | Val | Phe | Ile 345 | Asp | Tyr | Ala | His | Asn 350 | Gly | Asp |
| Ser | Leu | Lys 355 | Lys | Leu | Ile | Asn | Val 360 | Val | Glu | Thr | His | Gln 365 | Thr | Gly | Lys |
| Ile | Ala 370 | Leu | Val | Leu | Gly | Ser 375 | Thr | Gly | Asn | Lys | Gly 380 | Glu | Ser | Arg | Arg |
| Lys 385 | Asp | Phe | Gly | Leu | Leu 390 | Leu | Asn | Gln | His | Pro 395 | Glu | Ile | Gln | Val | Phe 400 |
| Leu | Thr | Ala | Asp | Asp 405 | Pro | Asn | Tyr | Glu | Asp 410 | Pro | Met | Ala | Ile | Ala 415 | Asp |
| Glu | Ile | Ser | Ser 420 | Tyr | Ile | Asn | His | Pro 425 | Val | Glu | Lys | Ile | Ala 430 | Asp | Arg |
| Gln | Glu | Ala 435 | Ile | Lys | Ala | Ala | Met 440 | Ala | Ile | Thr | Asn | His 445 | Glu | Leu | Asp |
| Ala | Val 450 | Ile | Ile | Ala | Gly | Lys 455 | Gly | Ala | Asp | Cys | Tyr 460 | Gln | Ile | Ile | Gln |
| Gly 465 | Lys | Lys | Glu | Ser | Tyr 470 | Pro | Gly | Asp | Thr | Ala 475 | Val | Ala | Glu | Asn | Tyr 480 |
| Leu | | | | | | | | | | | | | | | |

In a further embodiment the present invention relates to a ribonucleic acid molecule comprising the sequence identified as SEQ ID NO. 3:

```
AUGAUUAAGA UUGAAACCGU AUUAGAUAUU UUAAAGAAAG AUGGCCUUUU UCGCGAAAUU    60
AUUGACCAAG GUCAUUACCA CUACAACUAC AGCAAAGUUA UUUUUGAUAG CAUCAGCUAC   120
GACAGCCGAA AAGUAACAGA AGACACUCUU UUUUUUGCAA AAGGCGCUGC CUUUAAAAAA   180
GAAUACCUUC UUUCUGCUAU AACACAAGGU UUAGCUUGGU AUGUAGCUGA AAAGGACUAC   240
GAAGUCGAUA UCCCUGUCAU CAUUGUGAAC GAUAUAAAGA AAGCCAUGAG UUUGAUUGCC   300
AUGGAGUUCU AUGGUAAUCC ACAAGAGAAA CUCAAACUCC UUGCCUUUAC UGGUACUAAG   360
GGUAAGACAA CAGCAACCUA UUUCGCCUAU AACAUCUUAU CUCAAGGGCA UAGACCUGCU   420
AUGUUGUCGA CCAUGAACAC AACUCUUGAU GGCGAGACUU UCUUUAAGUC AGCGUUGACA   480
ACCCCUGAGA GUAUUGACCU CUUUGACAUG AUGAAUCAGG CUGUGCAAAA UGACCGUACC   540
CACCUCAUCA UGGAAGUCUC CAGUCAAGCC UAUCUAGUCC AUCGAGUCUA UGGACUGACC   600
UUUGAUGUAG GAGUCUUUCU UAACAUCACU CCUGACCAUA UCGGCCCGAU UGAACACCCU   660
AGCUUUGAAG ACUAUUUCUA CCACAAGCGU CUCUUGAUGG AAAAUAGCCG AGCAGUCAUC   620
AUUAACAGUG ACAUGGACCA CUUCUCAGUC UUGAAAGAAC AGGUUGAAGA UCAAGACCAU   780
GAUUUCUAUG GUAGCCAAUU UGAUAACCAA AUCGAGAAUU CCAAAGCCUU UAGCUUUUCA   840
GCUACGGGUA AACUCGCUGG AGAUUAUGAU AUCCAACUCA UUGGCAACUU CAACCAAGAA   900
```

```
AAUGCAGUUG CUGCUGGACU UGCUUGUCUC CGUCUCGGAG CAAGUCUUGA GGACAUCAAA    960

AAAGGCAUCG CUGCAACCCG CGUUCCUGGU CGUAUGGAAG UCCUCACUCA GAAAAAUGGA   1020

GCCAAGGUCU UCAUCGACUA UGCCCACAAU GGGGAUAGUC UGAAAAAACU CAUCAAUGUG   1080

GUUGAAACUC AUCAAACCGG AAAGAUUGCU CUGGUUCUGG GAUCAACAGG AAACAAGGGA   1140

GAAAGUCGUC GUAAGGACUU UGGCCUCCUC CUCAAUCAAC ACCCUGAGAU UCAAGUCUUU   1200

CUGACUGCUG AUGACCCUAA CUAUGAAGAC CCAAUGGCCA UUGCAGAUGA AAUUAGUAGC   1260

UACAUCAAUC AUCCUGUUGA AAAGAUUGCG GAUCGCCAAG AAGCCAUCAA GGCGGCAAUG   1320

GCUAUCACAA AUCACGAAUU AGAUGCAGUU AUUAUUGCGG GUAAGGGAGC CGAUUGUUAC   1380

CAAAUCAUCC AGGGCAAGAA AGAAUCCUAC CCAGGAGAUA CAGCCGUCGC AGAAAAUUAU   1440

UUAUAA
```

In yet another embodiment, the present invention is a recombinant DNA vector which incorporates the *Streptococcus pneumoniae* murE gene in operable linkage to gene expression sequences which enable the murE gene to be transcribed and translated in a host cell.

In still another embodiment the present invention relates to homologous or heterologous host cells which have been transformed or transfected with the cloned murE gene of *Streptococcus pneumoniae* such that the murE gene is expressed in the host cell.

In a still further embodiment, the present invention relates to a method for identifying inhibitory compounds which target the MurE protein of *Streptococcus pneumoniae*.

DESCRIPTION OF THE DRAWING

FIGURE. Plasmid pPSR10, which is useful for high level expression of the *Streptococcus pneumoniae* murE gene in heterologous or homologous procaryotic host cells.

DEFINITIONS

Figure 1:
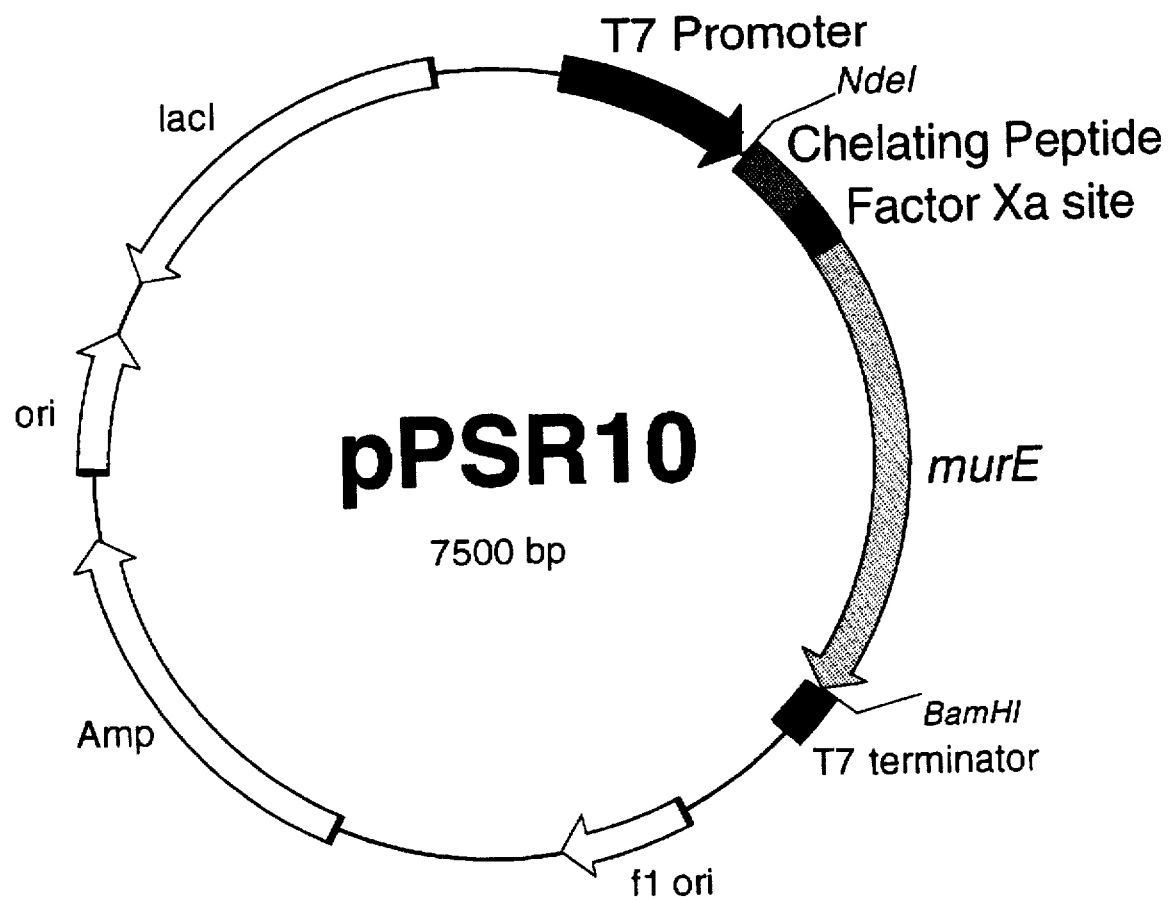

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "stringency" refers to a set of hybridization conditions which may be varied in order to vary the degree of nucleic acid hybridization with another nucleic acid.

DETAILED DESCRIPTION

The murE gene of *Streptococcus pneumoniae* encodes an enzyme involved in stem peptide biosynthesis. The stem peptide pathway is necessary for the synthesis of the peptidoglycan layer which is part of the bacterial cell wall. There are at least 10 steps involved in stem peptide biosynthesis. The murE gene encodes uridine-diphosphate-N-acetylmuramoyl-L-alanyl-D-glutamate:L-lysine ligase (SEQ ID NO. 2), which catalyzes the addition of L-lysine to UDPMurNAc-L-Ala-D-Glu forming UDPMurNAc-L-Ala-D-Glu-L-lys.

The murE gene of *Streptococcus pneumoniae* comprises a DNA sequence of 1443 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the gene may be obtained by a plurality of applicable genetic and recombinant DNA techniques including, for example, polymerase chain reaction (PCR) amplification, or de novo DNA synthesis.(See e.g., Sambrook et al. supra, Chap. 14)

Methods for constructing gene libraries in a suitable vector such as a plasmid or phage for propagation in procaryotic or eucaryotic cells are well known to those skilled in the art. [See e.g. J. Sambrook et al. *Molecular Cloning*, 2d Ed. (1989)]. Suitable cloning vectors are widely available. Skilled artisans will recognize that the murE gene of *Streptococcus pneumoniae* or fragment thereof could also be isolated by PCR amplification starting with *Streptococcus pneumoniae* genomic DNA and oligonucleotide primers targeted to any suitable region of SEQ ID NO. 1. Methods for PCR amplification are widely known in the art. See e.g. PCR *Protocols: a Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn. A positive result is determined by the presence of an appropriately-sized DNA fragment following agarose gel electrophoresis.

Protein Production Methods

One of the embodiments of the present invention is the purified protein encoded by the murE gene or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably –20° C. for thirty minutes followed by thirty minutes at 0° C.

The protein of the present invention can also be produced by recombinant DNA methods using the cloned murE gene of *Streptococcus pneumoniae*. Recombinant methods are preferred if a high yield is desired. Expression of the cloned murE gene can be carried out in a variety of suitable host cells well known to those skilled in the art. The murE gene is introduced into a host cell by any suitable means, well known to those skilled in the art. While chromosomal integration of the cloned murE gene is within the scope of the present invention, it is preferred that the gene be cloned into a suitable extra-chromosomally maintained expression vector so that the coding region of the murE gene is operably linked to a constitutive or inducible promoter.

The basic steps in the recombinant production of the MurE protein are:

a) constructing a natural, synthetic or semi-synthetic DNA encoding MurE protein;

b) integrating said DNA into an expression vector in a manner suitable for expressing the MurE protein, either alone or as a fusion protein;

c) transforming an appropriate eukaryotic or prokaryotic host cell with said expression vector, d) culturing said transformed host cell in a manner to express the MurE protein; and e) recovering and purifying the MurE protein by any suitable means.

Expressing Recombinant MurE Protein in Procaryotic and Eucaryotic Host Cells

In general, prokaryotes are used for cloning DNA sequences and for constructing the vectors of the present invention. Prokaryotes are also employed in the production of the MurE protein. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed in the cloning and expression of the proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to prokaryotes, mammalian host cells and eukaryotic microbes such as yeast may also be used. The simple eucaryote *Saccharomyces cerevisiae*, is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MurE Protein

An expression vector carrying the cloned murE gene of *Strepococcus pneumoniae* is transformed or transfected into a suitable host cell using standard methods. Cells which contain the vector are then propagated under conditions suitable for expression of the MurE protein. The recombinantly produced protein may be purified from cellular extracts of transformed cells by any suitable means. In a preferred process for protein purification the murE gene is modified at the 5' end to incorporate several histidine residues at the amino terminus of the MurE protein product. The histidine tag enables a single-step protein purification method referred to as "immobilized metal ion affinity chromatography" (IMAC), essentially as described in U.S. Pat. No. 4,569,794 which hereby is incorporated by reference.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The murE gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the murE gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

In an alternative methodology, murE DNA sequences comprising a portion or all of SEQ ID NO:1 can be generated from Streptococcus pneumoniae genomic DNA using suitable oligonucleotide primers complementary to SEQ ID NO:1 or region therein, utilizing the polymerase chain reaction as described in U.S. Pat. No. 4,889,818, which is incorporated herein by reference. Protocols for performing the PCR are disclosed in, *PCR Protocols: A Guide to Method and Applications*, Ed. Michael A. innis et al., Academic Press, Inc. (1990), which hereby is incorporated by reference.

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Streptococcus pneumoniae* DNA or mRNA encoding murE, is provided. Preferably, the 18 or more base pair compound is DNA.

These probes and primers can be prepared enzymatically as will be well known to those skilled in the art (See e.g. Sambrook et al. supra). In a most preferred embodiment these probes and primers are synthesized using chemical means as described above.

Another aspect of the present invention is recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence SEQ ID NO:1. Plasmid pPSR10 is an especially preferred DNA vector of the present invention.

The skilled artisan understands that choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers, metabolic markers, or the like), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they may be the basis for high level, regulatable expression of an operably linked gene. The skilled artisan will recognize a number of inducible promoters and inducers, for example, carbon source, metal ions, heat, and others. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pPSR10, which comprises SEQ ID NO:1. (See Figure). Transformed host cells may be cultured under conditions well known to skilled artisans such that SEQ ID NO:2 is expressed, thereby producing MurE protein in the recombinant host cell.

For the purpose of identifying or developing inhibitors of the stem peptide pathway, it would be desirable to determine those agents which inhibit the murE step. A method for determining whether a substance will inhibit the enzymatic reaction catalyzed by the MurE protein comprises contacting the MurE protein with a test substance and monitoring MurE enzyme activity by any suitable means.

The instant invention provides such a screening system useful for discovering agents which inhibit the MurE protein product, said screening system comprising the steps of:

a) preparing MurE enzyme;
b) exposing said MurE enzyme to a test inhibitor;
c) introducing substrate; and
d) quantifying the loss of activity of said MurE enzyme.

Utilization of the screening system described above provides a means to determine compounds which interfere with stem peptide biosynthesis. This screening system may be adapted to automated procedures such as a PANDEX® (Baxter-Dade Diagnostics) system allowing for efficient high-volume screening of potential therapeutic agents.

In such a screening protocol MurE enzyme is prepared as described herein, preferably using recombinant DNA technology. A sample of a test compound is then introduced into the reaction vessel containing the MurE enzyme, followed by the addition of enzyme substrate. In the alternative, the substrate may be added simultaneously with the test compound. For example, in a preferred method of the invention, radioactively or chemically-labeled substrate may be used. The products of the enzymatic reaction are then quantitated for the chemical label or radioactivity. The absence or diminution of the chemical label or radioactivity indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical development of drugs.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra.

The following examples more fully describe the present invention. Those skilled in the art will recognize that the particular reagents, equipment, and procedures described are merely illustrative and are not intended to limit the present invention in any manner.

EXAMPLE 1

Construction of DNA Vector for Expressing *Streptococcus pnuemoniae* murE Gene in Homologous or Heterologous Host Plasmid pPSR10 (See FIG. 1) is an approximately 7500 base pair expression vector suitable for expressing the murE gene of *S. pneumoniae* in the procaryotic host *E. coli*. This plasmid contains an origin of replication (Ori), an ampicillin resistance gene (Amp) useful for selecting cells which have incorporated the vector following a tranformation procedure, and further comprises the lacI gene for repression of the lac operon, as well as the T7 promoter and T7 terminator sequences in operable linkage to the coding region of the murE gene. Parent plasmid pET11A (obtained from Novogen, Madison, Wis.) was linearized by restriction with endonucleases NdeI and BamHI. Linearized pET11A was ligated to a DNA fragment bearing NdeI and BamHI sticky ends and comprising the coding region of the *S. pneumoniae* murE gene.

The murE gene ligated into pPSR10 was modified at the 5' end (amino terminus of encoded protein) in order to simplify purification of the encoded MurE protein product. For this purpose, an oligonucleotide encoding 8 histidine residues and a factor xa cleavage site was inserted after the ATG start codon at nucleotide positions 1 to 3 of SEQ ID NO: 1. Placement of the histidine residues at the amino terminus of the encoded protein does not affect its activity and serves only to enable the IMAC one-step protein purification procedure (See below).

EXAMPLE 2

Expression of *Streptococcus pneumoniae* murE Gene in *Echerichia coli* and Purification of MurE Enzyme Plasmid pPSR10 was transformed into *E. coli* BL21 (DE3)(hsdS gal λcIts857 ind1Sam7nin5lacUV5-T7gene 1) using standard methods. Transformants, selected for resistance to ampicillin, were chosen at random and tested for the presence of pPSR10 by agarose gel electrophoresis using quick plasmid preparations. Colonies which contained pPSR10 were grown in TY broth and the protein product encoded by the murE gene was purified by immobilized metal ion affinity chromatography (IMAC), essentially as described in U.S. Pat. No. 4,569,794, the entire contents of which is hereby incorporated by reference.

Briefly, the IMAC column was prepared as follows. A metal-free chelating resin (e.g. SEPHAROSE 6B IDA, Pharmacia) was washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin were saturated with colored metal ion. The column was then ready to receive a crude cellular extract containing the MurE protein product encoded by pPSR10.

After removing unbound proteins and other materials by washing the column with suitable buffer, pH 7.5, the bound protein was eluted in buffer at pH 4.3 essentially as described in U.S. Pat. No. 4,569,794.

EXAMPLE 3

Biochemical Assay for Inhibitors of *Streptococcus pneumoniae* MurE Enzyme Product The activity of the enzyme encoded by murE was assayed by monitoring the appearance of the enzyme product, UDP-MurNAc-L-Ala-D-Glu-L-Lys, using high-pressure liquid chromatography detection (HPLC). The enzyme reaction consisted of 0.1M Tris/HCl pH 8.6, 0.1M $MgCl_2$, 5 mM ATP, 50 µM UDP-MurNAc-L-Ala-D-Glu, 0.1 mM Lysine and enzyme in a final volume of 50 µl . Substrate UDP- MurNAc-L-Ala-D-Glu was purified as described in B. Flouret et al., *Reverse-phase high-pressure liquid chromatography of uridine diphosphate N-Acetylmuramyl peptide precursors of bacterial cell wall peptidoglycan*, Anal. Biochem. 114, 59–63 (1981). The mixture was incubated for 30 min. at 37° C., and the reaction terminated with the addition of 10 μl of glacial acetic acid. The amount of product generated was determined by HPLC, essentially as described in Flouret et.al.(Id.). Briefly, the nucleotide precursors were extracted in the cold by trichloroacetic acid and purified by gel filtration on fine SEPHADEX G-25. Under these conditions the UDP-MurNac derivatives are eluted with water in a volume slightly larger than the exclusion volume of the column. Separation and further purification of UDP-MurNAc derivatives were carried out by ion-exchange chromatography on Dowex AG1×2 (200–400 mesh) according to the method of Park & Chatterjee, *Methods in Enzmyology*, 8, 466–472 (Academic Press, New York 1966). HPLC analyses were performed with a Waters Associates apparatus consisting of two Model 6000 A solvent delivering systems, a Model 660 solvent programmer, and a Model 450 variable wavelength detector which monitored the eluant at 220 nm or at 262 nm. Peaks were recorded and integrated with a Spectra Physics SP 4100 model computing integrator (Spectra Physics, Santa Clara, Calif.).

Inhibition studies are carried out using the same reaction conditions described in the preceding paragraph. Compounds to be studied for inhibitory activity are added to final concentrations of between 1 mM and 10 mM.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1443

( x i ) SEQUENCE DESCRIPTION: SEQ ID NO:1:

```
ATG ATT AAG ATT GAA ACC GTA TTA GAT ATT TTA AAG AAA GAT GGC CTT      48
Met Ile Lys Ile Glu Thr Val Leu Asp Ile Leu Lys Lys Asp Gly Leu
 1               5                  10                  15

TTT CGC GAA ATT ATT GAC CAA GGT CAT TAC CAC TAC AAC TAC AGC AAA      96
Phe Arg Glu Ile Ile Asp Gln Gly His Tyr His Tyr Asn Tyr Ser Lys
            20                  25                  30

GTT ATT TTT GAT AGC ATC AGC TAC GAC AGC CGA AAA GTA ACA GAA GAC     144
Val Ile Phe Asp Ser Ile Ser Tyr Asp Ser Arg Lys Val Thr Glu Asp
        35                  40                  45

ACT CTT TTT TTT GCA AAA GGC GCT GCC TTT AAA AAA GAA TAC CTT CTT     192
Thr Leu Phe Phe Ala Lys Gly Ala Ala Phe Lys Lys Glu Tyr Leu Leu
    50                  55                  60

TCT GCT ATA ACA CAA GGT TTA GCT TGG TAT GTA GCT GAA AAG GAC TAC     240
Ser Ala Ile Thr Gln Gly Leu Ala Trp Tyr Val Ala Glu Lys Asp Tyr
65                  70                  75                  80

GAA GTC GAT ATC CCT GTC ATC ATT GTG AAC GAT ATA AAG AAA GCC ATG     288
Glu Val Asp Ile Pro Val Ile Ile Val Asn Asp Ile Lys Lys Ala Met
                85                  90                  95

AGT TTG ATT GCC ATG GAG TTC TAT GGT AAT CCA CAA GAG AAA CTC AAA     336
Ser Leu Ile Ala Met Glu Phe Tyr Gly Asn Pro Gln Glu Lys Leu Lys
            100                 105                 110

CTC CTT GCC TTT ACT GGT ACT AAG GGT AAG ACA ACA GCA ACC TAT TTC     384
Leu Leu Ala Phe Thr Gly Thr Lys Gly Lys Thr Thr Ala Thr Tyr Phe
        115                 120                 125

GCC TAT AAC ATC TTA TCT CAA GGG CAT AGA CCT GCT ATG TTG TCG ACC     432
Ala Tyr Asn Ile Leu Ser Gln Gly His Arg Pro Ala Met Leu Ser Thr
    130                 135                 140
```

| | | | | | | | | | | | | | | | | |
|---|---|---|---|---|---|---|---|---|---|---|---|---|---|---|---|---|
| ATG | AAC | ACA | ACT | CTT | GAT | GGC | GAG | ACT | TTC | TTT | AAG | TCA | GCG | TTG | ACA | 480 |
| Met | Asn | Thr | Thr | Leu | Asp | Gly | Glu | Thr | Phe | Phe | Lys | Ser | Ala | Leu | Thr | |
| 145 | | | | | 150 | | | | | 155 | | | | | 160 | |
| ACC | CCT | GAG | AGT | ATT | GAC | CTC | TTT | GAC | ATG | ATG | AAT | CAG | GCT | GTG | CAA | 528 |
| Thr | Pro | Glu | Ser | Ile | Asp | Leu | Phe | Asp | Met | Met | Asn | Gln | Ala | Val | Gln | |
| | | | | 165 | | | | | 170 | | | | | 175 | | |
| AAT | GAC | CGT | ACC | CAC | CTC | ATC | ATG | GAA | GTC | TCC | AGT | CAA | GCC | TAT | CTA | 576 |
| Asn | Asp | Arg | Thr | His | Leu | Ile | Met | Glu | Val | Ser | Ser | Gln | Ala | Tyr | Leu | |
| | | | 180 | | | | | 185 | | | | | 190 | | | |
| GTC | CAT | CGA | GTC | TAT | GGA | CTG | ACC | TTT | GAT | GTA | GGA | GTC | TTT | CTT | AAC | 624 |
| Val | His | Arg | Val | Tyr | Gly | Leu | Thr | Phe | Asp | Val | Gly | Val | Phe | Leu | Asn | |
| | | 195 | | | | | 200 | | | | | 205 | | | | |
| ATC | ACT | CCT | GAC | CAT | ATC | GGC | CCG | ATT | GAA | CAC | CCT | AGC | TTT | GAA | GAC | 672 |
| Ile | Thr | Pro | Asp | His | Ile | Gly | Pro | Ile | Glu | His | Pro | Ser | Phe | Glu | Asp | |
| | 210 | | | | | 215 | | | | | 220 | | | | | |
| TAT | TTC | TAC | CAC | AAG | CGT | CTC | TTG | ATG | GAA | AAT | AGC | CGA | GCA | GTC | ATC | 720 |
| Tyr | Phe | Tyr | His | Lys | Arg | Leu | Leu | Met | Glu | Asn | Ser | Arg | Ala | Val | Ile | |
| 225 | | | | | 230 | | | | | 235 | | | | | 240 | |
| ATT | AAC | AGT | GAC | ATG | GAC | CAC | TTC | TCA | GTC | TTG | AAA | GAA | CAG | GTT | GAA | 768 |
| Ile | Asn | Ser | Asp | Met | Asp | His | Phe | Ser | Val | Leu | Lys | Glu | Gln | Val | Glu | |
| | | | | 245 | | | | | 250 | | | | | 255 | | |
| GAT | CAA | GAC | CAT | GAT | TTC | TAT | GGT | AGC | CAA | TTT | GAT | AAC | CAA | ATC | GAG | 816 |
| Asp | Gln | Asp | His | Asp | Phe | Tyr | Gly | Ser | Gln | Phe | Asp | Asn | Gln | Ile | Glu | |
| | | | 260 | | | | | 265 | | | | | 270 | | | |
| AAT | TCC | AAA | GCC | TTT | AGC | TTT | TCA | GCT | ACG | GGT | AAA | CTC | GCT | GGA | GAT | 864 |
| Asn | Ser | Lys | Ala | Phe | Ser | Phe | Ser | Ala | Thr | Gly | Lys | Leu | Ala | Gly | Asp | |
| | | 275 | | | | | 280 | | | | | 285 | | | | |
| TAT | GAT | ATC | CAA | CTC | ATT | GGC | AAC | TTC | AAC | CAA | GAA | AAT | GCA | GTT | GCT | 912 |
| Tyr | Asp | Ile | Gln | Leu | Ile | Gly | Asn | Phe | Asn | Gln | Glu | Asn | Ala | Val | Ala | |
| | 290 | | | | | 295 | | | | | 300 | | | | | |
| GCT | GGA | CTT | GCT | TGT | CTC | CGT | CTC | GGA | GCA | AGT | CTT | GAG | GAC | ATC | AAA | 960 |
| Ala | Gly | Leu | Ala | Cys | Leu | Arg | Leu | Gly | Ala | Ser | Leu | Glu | Asp | Ile | Lys | |
| 305 | | | | | 310 | | | | | 315 | | | | | 320 | |
| AAA | GGC | ATC | GCT | GCA | ACC | CGC | GTT | CCT | GGT | CGT | ATG | GAA | GTC | CTC | ACT | 1008 |
| Lys | Gly | Ile | Ala | Ala | Thr | Arg | Val | Pro | Gly | Arg | Met | Glu | Val | Leu | Thr | |
| | | | | 325 | | | | | 330 | | | | | 335 | | |
| CAG | AAA | AAT | GGA | GCC | AAG | GTC | TTC | ATC | GAC | TAT | GCC | CAC | AAT | GGG | GAT | 1056 |
| Gln | Lys | Asn | Gly | Ala | Lys | Val | Phe | Ile | Asp | Tyr | Ala | His | Asn | Gly | Asp | |
| | | | 340 | | | | | 345 | | | | | 350 | | | |
| AGT | CTG | AAA | AAA | CTC | ATC | AAT | GTG | GTT | GAA | ACT | CAT | CAA | ACC | GGA | AAG | 1104 |
| Ser | Leu | Lys | Lys | Leu | Ile | Asn | Val | Val | Glu | Thr | His | Gln | Thr | Gly | Lys | |
| | | 355 | | | | | 360 | | | | | 365 | | | | |
| ATT | GCT | CTG | GTT | CTG | GGA | TCA | ACA | GGA | AAC | AAG | GGA | GAA | AGT | CGT | CGT | 1152 |
| Ile | Ala | Leu | Val | Leu | Gly | Ser | Thr | Gly | Asn | Lys | Gly | Glu | Ser | Arg | Arg | |
| | 370 | | | | | 375 | | | | | 380 | | | | | |
| AAG | GAC | TTT | GGC | CTC | CTC | CTC | AAT | CAA | CAC | CCT | GAG | ATT | CAA | GTC | TTT | 1200 |
| Lys | Asp | Phe | Gly | Leu | Leu | Leu | Asn | Gln | His | Pro | Glu | Ile | Gln | Val | Phe | |
| 385 | | | | | 390 | | | | | 395 | | | | | 400 | |
| CTG | ACT | GCT | GAT | GAC | CCT | AAC | TAT | GAA | GAC | CCA | ATG | GCC | ATT | GCA | GAT | 1248 |
| Leu | Thr | Ala | Asp | Asp | Pro | Asn | Tyr | Glu | Asp | Pro | Met | Ala | Ile | Ala | Asp | |
| | | | | 405 | | | | | 410 | | | | | 415 | | |
| GAA | ATT | AGT | AGC | TAC | ATC | AAT | CAT | CCT | GTT | GAA | AAG | ATT | GCG | GAT | CGC | 1296 |
| Glu | Ile | Ser | Ser | Tyr | Ile | Asn | His | Pro | Val | Glu | Lys | Ile | Ala | Asp | Arg | |
| | | | 420 | | | | | 425 | | | | | 430 | | | |
| CAA | GAA | GCC | ATC | AAG | GCG | GCA | ATG | GCT | ATC | ACA | AAT | CAC | GAA | TTA | GAT | 1344 |
| Gln | Glu | Ala | Ile | Lys | Ala | Ala | Met | Ala | Ile | Thr | Asn | His | Glu | Leu | Asp | |
| | | 435 | | | | | 440 | | | | | 445 | | | | |
| GCA | GTT | ATT | ATT | GCG | GGT | AAG | GGA | GCC | GAT | TGT | TAC | CAA | ATC | ATC | CAG | 1392 |
| Ala | Val | Ile | Ile | Ala | Gly | Lys | Gly | Ala | Asp | Cys | Tyr | Gln | Ile | Ile | Gln | |
| | 450 | | | | | 455 | | | | | 460 | | | | | |

```
GGC  AAG  AAA  GAA  TCC  TAC  CCA  GGA  GAT  ACA  GCC  GTC  GCA  GAA  AAT  TAT       1440
Gly  Lys  Lys  Glu  Ser  Tyr  Pro  Gly  Asp  Thr  Ala  Val  Ala  Glu  Asn  Tyr
465                 470                      475                      480

TTA  TAA                                                                              1446
Leu
```

( 2 ) INFORMATION FOR SEQ ID NO:2:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ile  Lys  Ile  Glu  Thr  Val  Leu  Asp  Ile  Leu  Lys  Lys  Asp  Gly  Leu
 1                    5                    10                     15

Phe  Arg  Glu  Ile  Ile  Asp  Gln  Gly  His  Tyr  His  Tyr  Asn  Tyr  Ser  Lys
               20                    25                     30

Val  Ile  Phe  Asp  Ser  Ile  Ser  Tyr  Asp  Ser  Arg  Lys  Val  Thr  Glu  Asp
                35                     40                    45

Thr  Leu  Phe  Phe  Ala  Lys  Gly  Ala  Ala  Phe  Lys  Lys  Glu  Tyr  Leu  Leu
      50                     55                    60

Ser  Ala  Ile  Thr  Gln  Gly  Leu  Ala  Trp  Tyr  Val  Ala  Glu  Lys  Asp  Tyr
 65                    70                    75                          80

Glu  Val  Asp  Ile  Pro  Val  Ile  Ile  Val  Asn  Asp  Ile  Lys  Lys  Ala  Met
                     85                    90                          95

Ser  Leu  Ile  Ala  Met  Glu  Phe  Tyr  Gly  Asn  Pro  Gln  Glu  Lys  Leu  Lys
                100                      105                    110

Leu  Leu  Ala  Phe  Thr  Gly  Thr  Lys  Gly  Lys  Thr  Thr  Ala  Thr  Tyr  Phe
           115                     120                     125

Ala  Tyr  Asn  Ile  Leu  Ser  Gln  Gly  His  Arg  Pro  Ala  Met  Leu  Ser  Thr
      130                     135                     140

Met  Asn  Thr  Thr  Leu  Asp  Gly  Glu  Thr  Phe  Phe  Lys  Ser  Ala  Leu  Thr
145                      150                     155                      160

Thr  Pro  Glu  Ser  Ile  Asp  Leu  Phe  Asp  Met  Met  Asn  Gln  Ala  Val  Gln
                     165                     170                     175

Asn  Asp  Arg  Thr  His  Leu  Ile  Met  Glu  Val  Ser  Ser  Gln  Ala  Tyr  Leu
           180                     185                     190

Val  His  Arg  Val  Tyr  Gly  Leu  Thr  Phe  Asp  Val  Gly  Val  Phe  Leu  Asn
      195                     200                     205

Ile  Thr  Pro  Asp  His  Ile  Gly  Pro  Ile  Glu  His  Pro  Ser  Phe  Glu  Asp
210                      215                     220

Tyr  Phe  Tyr  His  Lys  Arg  Leu  Leu  Met  Glu  Asn  Ser  Arg  Ala  Val  Ile
225                      230                     235                      240

Ile  Asn  Ser  Asp  Met  Asp  His  Phe  Ser  Val  Leu  Lys  Glu  Gln  Val  Glu
                     245                     250                     255

Asp  Gln  Asp  His  Asp  Phe  Tyr  Gly  Ser  Gln  Phe  Asp  Asn  Gln  Ile  Glu
           260                     265                     270

Asn  Ser  Lys  Ala  Phe  Ser  Phe  Ser  Ala  Thr  Gly  Lys  Leu  Ala  Gly  Asp
      275                     280                     285

Tyr  Asp  Ile  Gln  Leu  Ile  Gly  Asn  Phe  Asn  Gln  Glu  Asn  Ala  Val  Ala
      290                     295                     300

Ala  Gly  Leu  Ala  Cys  Leu  Arg  Leu  Gly  Ala  Ser  Leu  Glu  Asp  Ile  Lys
305                      310                     315                      320

Lys  Gly  Ile  Ala  Ala  Thr  Arg  Val  Pro  Gly  Arg  Met  Glu  Val  Leu  Thr
```

|     |     |     |     | 325 |     |     |     |     | 330 |     |     |     |     | 335 |
| --- | --- | --- | --- | --- | --- | --- | --- | --- | --- | --- | --- | --- | --- | --- |
| Gln | Lys | Asn | Gly | Ala | Lys | Val | Phe | Ile | Asp | Tyr | Ala | His | Asn | Gly | Asp |
|     |     |     | 340 |     |     |     |     | 345 |     |     |     |     | 350 |     |     |
| Ser | Leu | Lys | Lys | Leu | Ile | Asn | Val | Val | Glu | Thr | His | Gln | Thr | Gly | Lys |
|     |     | 355 |     |     |     |     | 360 |     |     |     |     | 365 |     |     |     |
| Ile | Ala | Leu | Val | Leu | Gly | Ser | Thr | Gly | Asn | Lys | Gly | Glu | Ser | Arg | Arg |
|     | 370 |     |     |     |     | 375 |     |     |     |     | 380 |     |     |     |     |
| Lys | Asp | Phe | Gly | Leu | Leu | Leu | Asn | Gln | His | Pro | Glu | Ile | Gln | Val | Phe |
| 385 |     |     |     |     | 390 |     |     |     |     | 395 |     |     |     |     | 400 |
| Leu | Thr | Ala | Asp | Asp | Pro | Asn | Tyr | Glu | Asp | Pro | Met | Ala | Ile | Ala | Asp |
|     |     |     |     | 405 |     |     |     |     | 410 |     |     |     |     | 415 |     |
| Glu | Ile | Ser | Ser | Tyr | Ile | Asn | His | Pro | Val | Glu | Lys | Ile | Ala | Asp | Arg |
|     |     |     | 420 |     |     |     |     | 425 |     |     |     |     | 430 |     |     |
| Gln | Glu | Ala | Ile | Lys | Ala | Ala | Met | Ala | Ile | Thr | Asn | His | Glu | Leu | Asp |
|     |     |     | 435 |     |     |     |     | 440 |     |     |     |     | 445 |     |     |
| Ala | Val | Ile | Ile | Ala | Gly | Lys | Gly | Ala | Asp | Cys | Tyr | Gln | Ile | Ile | Gln |
|     | 450 |     |     |     |     | 455 |     |     |     |     | 460 |     |     |     |     |
| Gly | Lys | Lys | Glu | Ser | Tyr | Pro | Gly | Asp | Thr | Ala | Val | Ala | Glu | Asn | Tyr |
| 465 |     |     |     |     | 470 |     |     |     |     | 475 |     |     |     |     | 480 |
| Leu |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

```
AUGAUUAAGA UUGAAACCGU AUUAGAUAUU UUAAAGAAAG AUGGCCUUUU UCGCGAAAUU      60
AUUGACCAAG GUCAUUACCA CUACAACUAC AGCAAAGUUA UUUUUGAUAG CAUCAGCUAC     120
GACAGCCGAA AAGUAACAGA AGACACUCUU UUUUUUGCAA AAGGCGCUGC CUUUAAAAAA     180
GAAUACCUUC UUUCUGCUAU AACACAAGGU UUAGCUUGGU AUGUAGCUGA AAAGGACUAC     240
GAAGUCGAUA UCCCUGUCAU CAUUGUGAAC GAUAUAAAGA AAGCCAUGAG UUUGAUUGCC     300
AUGGAGUUCU AUGGUAAUCC ACAAGAGAAA CUCAAACUCC UUGCCUUUAC UGGUACUAAG     360
GGUAAGACAA CAGCAACCUA UUUCGCCUAU AACAUCUUAU CUCAAGGGCA UAGACCUGCU     420
AUGUUGUCGA CCAUGAACAC AACUCUUGAU GGCGAGACUU UCUUUAAGUC AGCGUUGACA     480
ACCCCUGAGA GUAUUGACCU CUUUGACAUG AUGAAUCAGG CUGUGCAAAA UGACCGUACC     540
CACCUCAUCA UGGAAGUCUC CAGUCAAGCC UAUCUAGUCC AUCGAGUCUA UGGACUGACC     600
UUUGAUGUAG GAGUCUUUCU UAACAUCACU CCUGACCAUA UCGGCCCGAU UGAACACCCU     660
AGCUUUGAAG ACUAUUUCUA CCACAAGCGU CUCUUGAUGG AAAAUAGCCG AGCAGUCAUC     720
AUUAACAGUG ACAUGGACCA CUUCUCAGUC UUGAAAGAAC AGGUUGAAGA UCAAGACCAU     780
GAUUUCUAUG GUAGCCAAUU UGAUAACCAA AUCGAGAAUU CCAAAGCCUU UAGCUUUUCA     840
GCUACGGGUA AACUCGCUGG AGAUUAUGAU AUCCAACUCA UUGGCAACUU CAACCAAGAA     900
AAUGCAGUUG CUGCUGGACU UGCUUGUCUC CGUCUCGGAG CAAGUCUUGA GGACAUCAAA     960
AAAGGCAUCG CUGCAACCCG CGUUCCUGGU CGUAUGGAAG UCCUCACUCA GAAAAAUGGA    1020
GCCAAGGUCU UCAUCGACUA UGCCCACAAU GGGGAUAGUC UGAAAAAACU CAUCAAUGUG    1080
```

| | | | | | | |
|---|---|---|---|---|---|---|
| GUUGAAACUC | AUCAAACCGG | AAAGAUUGCU | CUGGUUCUGG | GAUCAACAGG | AAACAAGGGA | 1140 |
| GAAAGUCGUC | GUAAGGACUU | UGGCCUCCUC | CUCAAUCAAC | ACCCUGAGAU | UCAAGUCUUU | 1200 |
| CUGACUGCUG | AUGACCCUAA | CUAUGAAGAC | CCAAUGGCCA | UUGCAGAUGA | AAUUAGUAGC | 1260 |
| UACAUCAAUC | AUCCUGUUGA | AAAGAUUGCG | GAUCGCCAAG | AAGCCAUCAA | GGCGGCAAUG | 1320 |
| GCUAUCACAA | AUCACGAAUU | AGAUGCAGUU | AUUAUUGCGG | GUAAGGGAGC | CGAUUGUUAC | 1380 |
| CAAAUCAUCC | AGGGCAAGAA | AGAAUCCUAC | CCAGGAGAUA | CAGCCGUCGC | AGAAAAUUAU | 1440 |
| UUAUAA | | | | | | 1446 |

We claim:

1. A substantially pure MurE protein from *Streptococcus pneumoniae* having the amino acid sequence which is SEQ ID NO:2.

2. A method for identifying inhibitory compounds of *Streptococcus pneumoniae* MurE protein activity, comprising the steps of:
   a) admixing in a suitable reaction buffer
      i) a substantially pure MurE protein as claimed in claim 1;
      ii) a suitable substrate;
      iii) a test inhibitory compound;
   b) measuring by any suitable means the amount of product formed; and
   c) comparing the amount of product formed with a control in which no test inhibitory compound is present.

3. A method, as in claim 2 wherein the substrate of step (a) (ii) comprises UDP-MurNAc-L-Ala-D-Glu.

4. A method, as in claim 2 wherein the amount of product formed at step (b) is determined by HPLC.

5. A kit useful for identifying inhibitors of stem peptide biosynthesis said kit comprising:
   a) a substantially pure MurE protein, as claimed in claim 1; and
   b) a suitable substrate for said protein.

* * * * *